US008409630B2

(12) United States Patent
Moore, Jr. et al.

(10) Patent No.: US 8,409,630 B2
(45) Date of Patent: *Apr. 2, 2013

(54) CONTINUOUS PROCESSES FOR PREPARING CONCENTRATED AQUEOUS LIQUID BIOCIDAL COMPOSITIONS

(75) Inventors: Robert M. Moore, Jr., Baton Rouge, LA (US); Christopher J. Nalepa, Baton Rouge, LA (US)

(73) Assignee: Albermarle Corporation, Baton Rouge, LA (US)

( * ) Notice: Subject to any disclaimer, the term of this patent is extended or adjusted under 35 U.S.C. 154(b) by 2357 days.

This patent is subject to a terminal disclaimer.

(21) Appl. No.: 09/785,890

(22) Filed: Feb. 16, 2001

(65) Prior Publication Data

US 2001/0004461 A1  Jun. 21, 2001

Related U.S. Application Data

(63) Continuation of application No. 09/451,344, filed on Nov. 30, 1999, now Pat. No. 6,352,725, which is a continuation-in-part of application No. 09/442,025, filed on Nov. 17, 1999, now Pat. No. 6,306,441, which is a continuation-in-part of application No. 09/088,300, filed on Jun. 1, 1998, now Pat. No. 6,068,861.

(51) Int. Cl.
*A01N 59/02* (2006.01)
*A61K 31/185* (2006.01)
(52) U.S. Cl. ........................................ 424/711; 514/578
(58) Field of Classification Search .................. 424/703
See application file for complete search history.

(56) References Cited

U.S. PATENT DOCUMENTS

| | | | |
|---|---|---|---|
| 1,995,639 A | 3/1935 | Henderson | |
| 2,184,886 A | 12/1939 | Muskat et al. | |
| 2,184,888 A | 12/1939 | Muskat et al. | |
| 2,443,429 A | 6/1948 | Marks | |
| 2,580,808 A | 1/1952 | Marks et al. | |
| 2,662,855 A | 12/1953 | Kamlett | |
| 2,779,764 A | 1/1957 | Paterson | |
| 2,815,311 A | 12/1957 | Ellis et al. | |
| 2,913,460 A | 11/1959 | Brown et al. | |
| 2,929,816 A | 2/1960 | Chamberlain | |
| 2,971,959 A | 2/1961 | Waugh et al. | |
| 3,147,254 A | 9/1964 | Paterson | |
| 3,147,259 A | 9/1964 | Paterson | |
| 3,152,073 A | 10/1964 | Morton | |
| 3,170,883 A | 2/1965 | Owen et al. | |
| 3,222,276 A | 12/1965 | Belohlav et al. | |
| 3,308,062 A | 3/1967 | Gunther | |
| 3,328,294 A | 6/1967 | Self et al. | |
| 3,412,021 A | 11/1968 | Paterson | |
| 3,429,668 A | 2/1969 | Gaska et al. | |
| 3,519,569 A | 7/1970 | Diaz | |
| 3,558,503 A * | 1/1971 | Goodenough et al. | 252/187.2 |
| 3,589,859 A | 6/1971 | Foroulis | |
| 3,711,246 A | 1/1973 | Foroulis | |
| 3,749,672 A | 7/1973 | Golton et al. | |
| 3,767,586 A | 10/1973 | Rutkiewic | |
| 3,850,833 A | 11/1974 | Koceich et al. | |
| 4,032,460 A | 6/1977 | Zilch et al. | |
| 4,235,599 A | 11/1980 | Davis et al. | |
| 4,237,090 A | 12/1980 | DeMonbrun et al. | |
| 4,295,932 A | 10/1981 | Pocius | |
| 4,297,224 A | 10/1981 | Macchiarolo et al. | |
| 4,382,799 A | 5/1983 | Davis et al. | 8/107 |
| 4,392,799 A | 7/1983 | Shikano et al. | |
| 4,427,435 A | 1/1984 | Lorenz et al. | |
| 4,451,376 A | 5/1984 | Sharp | |
| 4,465,598 A | 8/1984 | Darlington et al. | |
| 4,476,930 A | 10/1984 | Watanabe | |
| 4,490,308 A | 12/1984 | Fong et al. | |
| 4,491,507 A | 1/1985 | Herklotz et al. | |
| 4,539,071 A | 9/1985 | Clifford et al. | |
| 4,546,156 A | 10/1985 | Fong et al. | |
| 4,557,926 A | 12/1985 | Nelson et al. | |
| 4,566,973 A | 1/1986 | Masler, III et al. | |
| 4,595,517 A | 6/1986 | Abadi | |
| 4,595,691 A | 6/1986 | LaMarre et al. | 514/367 |
| 4,604,431 A | 8/1986 | Fong et al. | |

(Continued)

FOREIGN PATENT DOCUMENTS

| | | |
|---|---|---|
| EP | 1 080 641 A2 | 3/2001 |
| GB | 644 | 0/1910 |

(Continued)

OTHER PUBLICATIONS

Declaration of B. Gary McKinnie, 368047 (Exhibit 1001). The Second Declaration of B. Gary McKinnie, Feb. 14, 2005 (Exhibit 1073).*

(Continued)

*Primary Examiner* — Alton Pryor
(74) *Attorney, Agent, or Firm* — Marcy M. Hoefling

(57) ABSTRACT

The process involves (a) continuously forming bromine chloride from separate feed streams of bromine and chlorine by maintaining said streams under automatic feed rate control whereby the streams are continuously proportioned to come together in equimolar amounts to form bromine chloride; (b) continuously forming an aqueous product having an active bromine content of at least 100,000 ppm (wt/wt), a pH of at least 7, and an atom ratio of nitrogen to active bromine greater than 0.93:1 by continuously feeding into mixing apparatus separate feed streams of (1) bromine chloride formed in (a), and (2) an aqueous solution of alkali metal salt of sulfamic acid, under automatic feed rate control whereby the feed streams are continuously proportioned to come together in amounts that produce an aqueous product having an active bromine content of at least 100,000 ppm (wt/wt), a pH of at least 7, and an atom ratio of nitrogen to active bromine from (1) and (2) greater than 0.93:1; and, (c) withdrawing said aqueous product from said mixing apparatus at a rate sufficient to enable the continuous feeding in (a) and (b) to be maintained.

10 Claims, 3 Drawing Sheets

U.S. PATENT DOCUMENTS

| | | | |
|---|---|---|---|
| 4,642,194 A | 2/1987 | Johnson | |
| 4,643,835 A | 2/1987 | Koeplin-Gall et al. | |
| 4,661,503 A | 4/1987 | Martin et al. | |
| 4,680,339 A | 7/1987 | Fong | |
| 4,680,399 A | 7/1987 | Buchardt | 546/139 |
| 4,703,092 A | 10/1987 | Fong | |
| 4,711,724 A | 12/1987 | Johnson | |
| 4,752,443 A | 6/1988 | Hoots et al. | |
| 4,759,852 A | 7/1988 | Trulear | |
| 4,762,894 A | 8/1988 | Fong et al. | |
| 4,777,219 A | 10/1988 | Fong | |
| 4,801,388 A | 1/1989 | Fong et al. | |
| 4,802,990 A | 2/1989 | Inskeep, Jr. | |
| 4,822,513 A | 4/1989 | Corby et al. | |
| 4,846,979 A | 7/1989 | Hamilton | |
| 4,872,999 A | 10/1989 | Schild et al. | |
| 4,883,600 A | 11/1989 | MacDonald et al. | |
| 4,886,915 A | 12/1989 | Favstritsky | |
| 4,898,686 A | 2/1990 | Johnson et al. | |
| 4,906,651 A | 3/1990 | Hsu | |
| 4,923,634 A | 5/1990 | Hoots et al. | |
| 4,929,424 A | 5/1990 | Meier et al. | |
| 4,929,425 A | 5/1990 | Hoots et al. | |
| 4,966,716 A | 10/1990 | Favstritsky et al. | |
| 4,992,209 A | 2/1991 | Smyk et al. | |
| 4,995,987 A | 2/1991 | Whitekettle et al. | |
| 5,034,155 A | 7/1991 | Soeder et al. | |
| 5,035,806 A | 7/1991 | Fong et al. | |
| 5,047,164 A | 9/1991 | Corby et al. | |
| 5,055,285 A | 10/1991 | Duncan et al. | |
| 5,118,426 A | 6/1992 | Duncan et al. | |
| 5,120,452 A | 6/1992 | Ness et al. | |
| 5,120,797 A | 6/1992 | Fong et al. | |
| 5,130,033 A | 7/1992 | Thornhill et al. | |
| 5,141,652 A | 8/1992 | Moore, Jr. et al. | |
| 5,179,173 A | 1/1993 | Fong et al. | |
| 5,192,459 A | 3/1993 | Tell et al. | |
| 5,194,238 A | 3/1993 | Duncan et al. | |
| 5,196,126 A | 3/1993 | O'Dowd et al. | |
| 5,202,047 A | 4/1993 | Corby et al. | |
| 5,209,934 A | 5/1993 | Ekis, Jr. et al. | |
| 5,259,985 A | 11/1993 | Nakanishi et al. | |
| 5,264,136 A | 11/1993 | Howarth et al. | |
| 5,389,384 A | 2/1995 | Jooste et al. | |
| 5,414,652 A | 5/1995 | Mieda et al. | |
| 5,424,032 A | 6/1995 | Christensen et al. | |
| 5,429,723 A | 7/1995 | Atkinson et al. | |
| 5,443,849 A | 8/1995 | Corby et al. | |
| 5,460,833 A | 10/1995 | Andrews et al. | |
| 5,464,636 A | 11/1995 | Hight et al. | |
| 5,525,241 A | 6/1996 | Clavin et al. | |
| 5,527,547 A | 6/1996 | Hight et al. | |
| 5,565,109 A | 10/1996 | Sweeny | |
| 5,589,106 A | 12/1996 | Shim et al. | |
| 5,607,619 A | 3/1997 | Dadgar et al. | |
| 5,679,239 A | 10/1997 | Blum et al. | |
| 5,683,654 A * | 11/1997 | Dallmier et al. | 422/14 |
| 5,688,515 A | 11/1997 | Kuechler et al. | |
| 5,795,487 A | 8/1998 | Dallmier et al. | |
| 5,900,512 A | 5/1999 | Elnagar et al. | |
| 5,922,745 A | 7/1999 | McCarthy et al. | |
| 5,942,126 A | 8/1999 | Dallmier et al. | |
| 6,007,726 A | 12/1999 | Yang et al. | |
| 6,015,782 A | 1/2000 | Petri et al. | |
| 6,037,318 A | 3/2000 | Na et al. | |
| 6,068,861 A * | 5/2000 | Moore et al. | 424/703 |
| 6,069,142 A | 5/2000 | Gaffney et al. | |
| 6,086,861 A | 7/2000 | Onitsuka et al. | |
| 6,110,387 A | 8/2000 | Choudhury et al. | |
| 6,123,870 A | 9/2000 | Yang et al. | |
| 6,136,205 A | 10/2000 | Dallmier et al. | |
| 6,156,229 A | 12/2000 | Yang et al. | |
| 6,270,722 B1 | 8/2001 | Yang et al. | |
| 6,287,473 B1 | 9/2001 | Yang et al. | |
| 6,299,909 B1 | 10/2001 | Moore, Jr. et al. | |
| 6,306,441 B1 | 10/2001 | Moore, Jr. et al. | |
| 6,322,749 B1 | 11/2001 | McCarthy et al. | |
| 6,322,822 B1 | 11/2001 | Moore, Jr. et al. | |
| 6,348,219 B1 | 2/2002 | Torres et al. | |
| 6,352,725 B1 | 3/2002 | Torres et al. | |
| 6,375,991 B1 | 4/2002 | Moore, Jr. | |
| 6,419,879 B1 | 7/2002 | Cooper et al. | |
| 6,423,267 B1 | 7/2002 | Yang et al. | |
| 6,471,974 B1 | 10/2002 | Rees et al. | |
| 6,478,972 B1 | 11/2002 | Shim et al. | |
| 6,506,418 B1 | 1/2003 | McKinnie et al. | |
| 6,511,682 B1 | 1/2003 | Moore, Jr. et al. | |
| 6,533,958 B2 | 3/2003 | Shim et al. | |
| 6,652,889 B2 * | 11/2003 | Moore et al. | 424/703 |
| 6,660,307 B2 | 12/2003 | Zolotarsky et al. | |
| 6,669,904 B1 | 12/2003 | Yang et al. | |
| 6,740,253 B2 | 5/2004 | Vohra et al. | |
| 7,087,251 B2 * | 8/2006 | Nalepa | 424/703 |
| 7,195,782 B2 * | 3/2007 | Moore et al. | 424/703 |
| 7,204,931 B2 | 4/2007 | Martin et al. | |
| 2001/0004461 A1 | 6/2001 | Moore, Jr. et al. | |
| 2004/0022874 A1 * | 2/2004 | Nalepa et al. | 424/723 |
| 2004/0120853 A1 * | 6/2004 | Carpenter et al. | 422/37 |
| 2005/0061197 A1 * | 3/2005 | Nalepa | 106/15.05 |
| 2005/0147696 A1 * | 7/2005 | Moore et al. | 424/723 |
| 2006/0278586 A1 | 12/2006 | Nalepa et al. | |

FOREIGN PATENT DOCUMENTS

| | | |
|---|---|---|
| GB | 365558 | 1/1932 |
| GB | 526952 | 9/1940 |
| GB | 763383 | 12/1956 |
| GB | 1355359 | 6/1974 |
| GB | 2302687 | 1/1997 |
| RU | 2082659 C1 | 6/1997 |
| WO | WO-89/10696 | 11/1989 |
| WO | 9015780 | 12/1990 |
| WO | WO-90/15780 | 12/1990 |
| WO | WO 96/14092 A1 | 5/1996 |
| WO | WO-96/14092 A1 | 5/1996 |
| WO | WO-96/30562 | 10/1996 |
| WO | 9720546 | 6/1997 |
| WO | 9720909 | 6/1997 |
| WO | WO-97/20546 | 6/1997 |
| WO | WO-97/20909 | 6/1997 |
| WO | 9734827 | 9/1997 |
| WO | WO-97/34827 | 9/1997 |
| WO | 9743392 | 11/1997 |
| WO | WO-97/43392 | 11/1997 |
| WO | 9815609 | 4/1998 |
| WO | WO-98/15609 | 4/1998 |
| WO | 9906320 | 2/1999 |
| WO | WO-99/06320 | 2/1999 |
| WO | 9932596 | 7/1999 |
| WO | WO-99/32596 | 7/1999 |
| WO | 9955627 | 11/1999 |
| WO | WO-99/55627 | 11/1999 |
| WO | WO-99/62339 | 12/1999 |
| WO | 00/34186 | 6/2000 |
| WO | WO-00/34186 | 6/2000 |
| WO | WO-00/58532 | 10/2000 |
| WO | WO-03/093171 A1 | 11/2003 |

OTHER PUBLICATIONS

Mills et al., Bromine Chloride: an Alternativel to Bromine, Ind. Eng. Chem. Prod. Res. Develop., vol. 12, No. 3, 1973, pp. 160-165 (Exhibit 2014).*

Declaration of Dr. Jack Mills, Dec. 6, 2004 (Exhibit 2021). Expert Declaration of Dr. Shunong Yang, Dec. 6, 2004 (Exhibit 2022).*

Expert Declaration of John A. Wojtowicz, Dec. 7, 2004 (Exhibit 2023).*

Willard et al., "Elementary Quantitative Analysis", Third Edition, Chapter XIV—Oxidation and Reduction Processes Involving Iodine (Iodometry) 1940ppg. 261-271.

W. Büchner et al., *Industrial Inorganic Chemistry*, p. 180 (1989).

M.W. Lister, Decomposition of Sodium Hypochlorite: The Uncatalyzed Reaction,. pp. 465, 473-476, and 478 (1956).

F.A. Cotton et al., Advanced Inorganic Chemistry, p. 566 (1999).

J.F. Mills, *The Chemistry of Bromine Chloride in Waste Water Disinfection*, Paper Presented to the American Chemical Society Division of Water, Air, and Waste Chemicals (Aug. 1973).

Dow Chemical Company, Dow BrCl Newsletter (Inorganic Chemicals Dept.) (Jul. 1979).
J.F. Mills et al., *Bromine Chloride: An Alternative to Bromine*, Ind. Eng. Chem. Prod. Res. Develop., vol. 12, No. 3 pp. 160-165 (1973).
Z.E. Jolles, *Bromine and its Compounds*, pp. 68, 364, 365 (1966).
Z.E. Jolles, *Bromine and its Compounds*, p. 30 (1966).
Clare, A.S., "Marine Natural Product Antifoulants: Status and Potential," Biofouling (1996) 9:211-229.
S. Tsukamoto, et al., "Ceratinimides A and B: New Antifouling Dibromotyrosine Derivatives from the Marine Sponge *Pseudoceratina purpurea*," Tetrahedron (1996) 52: 8181-8186.
W. Miki, K. Kon-ya, and S. Mizobuchi, "*Biofouling and Marine Biotechnology: New Antifoulants from Marine Invertebrates*,": Journal of Marine Biotechnology (1996) 4: 117-120.
H. Genthe, "*The Incredible Sponge*," Smithsonian (Aug. 1998) 29: 50-58.
M. Givskov, et al., "Eukaryotic Interference with Homoierine Lactone-Mediated Prokaryotic Signaling," Journal of Bacteriology (1996) 178: 6618-6622.
F.W. Tanner and G. Pitner, "*Germicidal Action of Bromine*," Proceedings of the Society for Experimental Biology and Medicine (1939) 40: 143-145.
T. Kristoffersen and I.A. Gould. "Effect of Sodium Bromide on the Bactericidal Effectiveness of Hypochlorite Sanitizers of High Alkainity," Journal of Dairy Science (1958) 41: 950-955.
"Legionellosis Guideline: Best Practices for Control of *Legionella*," (Houston, TX: Cooling Tower Institute, Feb. 2000), 8 pages.
W.A. Brungs, "*Effects of Residual Chlorine on Aquatic Life*," Journal of the Water Pollution Control Federation (1973) 45: 2180-2193.
D. Vanderpool, M. Killoran, and R. Sergent, "*Improving the Corrosion Inhibitor Efficiency of Tolyltriazole in the Presence of Chlorine and Bromine*," paper 157 (Corrosion 87, San Francisco, CA, 1987), pp. 157/1-157/9.
B.R. Sook, T.F. Ling, and A.D. Harrison "*A New Thixotropic Form of Bromochlorodimethylhydantoin: A Case Study*," paper 03715 (Corrosion 2003, Houston, TX: NACE International, 2003), pp. 1-16.
D. Ren, J.J. Sims, and T.K. Wood, "Inhibition of Biofilm Formation and Swarming of *Bacillus subtilus* by (5Z)-4-Bromo-5-(Bromomethylene)-3-Butyl-2(5H)-Furanone," Letters in Applied Microbiology (2002) 34: 293-299.
J.A. McCarthy, Journal of the New England Water Works Association (1944) 58: 55-68.
G.U. Houghton, "The Bromine Content of Underground Waters. Part II. Observations on the Chlorination of Water Containing Free Ammonia and Naturally Occuring Bromide", Journal of the Society of the Chemical Industry (1946) 65: 324-328.
M.E. Weeks, "*The Discovery of the Elements: XVII. The Halogen Family*," Journal of Chemical Education (1932) 9: 1915-1939.
A.J. Balard, *Annales de Chemie et de Physique* (1826), vol. 32, pp. 371-372.
H.S. Rzepa, "Elemental and Molecular Heritage: An Internet-Based Display," Molecules (1998) 3: 94-99.
B. Grinbaum and M. Friedman, "Bromine," In *Kirk-Othmer Encyclopedia of Chemical Technology* 4th Ed. (New York, NY: John Wiley and Sons, Inc. 2001), vol. 4, pp. 548-549.
F. Yaron, "Bromine Manufacture: Technology and Economic Aspects," in "*Bromine and Its Compounds*," Z.E. Jolles, ed., pp. 3-11, and 41 (New York, NY: Academic Press, 1966).
"Bromine Brine," Arkansas Geological Commission, web address www.state.ar.us/agc/bromlne.htm; 1 page.
R. D. Bartholomew, "*Bromine-based Biocides for Cooling Water Systems: A Literature Review*," Paper IWC 98-74 (Pittsburgh, PA: Engineers' Society of Western Pennysivanle, 1998), 30 pages.
T.D. Beckwith and J.R. Moser, Journal of the American Water Works Association (1933) 25: 367-374.
D.R. Wood and E.T. Illing, Analyst (1930), Royal Society of Chemistry, The Analyst, 55: 125-126.
O. Wyss and R.J. Stockton, "*The Germicidal Action of Bromine*," Arch. Biochem. (1947) 12:267-271.
E.A. Shilov and J. N. Gladtchikova, "*On the Calculation of the Dissociation Constants of Hypohalogenous Acids from Kinetic Data*," Journal of the American Chemical Society (1938) 60: 490-491.

G.M. Fair, et al., "*The Behavior of Chlorine as 'A Water Disinfectant*," Journal of the American Water Works Association (1948) 40: 105.1-1061.
E.K Rideal and U.R. Evans, "*The Effect of Alkalinity on the Use of Hypochlorites*," Journal of the Society of the Chemical Industry. (1921) 40: 64R-66R.
C.K. Johns, "*Germicidal Power of Sodium. Hypochlorite*," Industrial' and Engineering Chemistry (1934) 26: 787-788.
G.R. Dychala, "Chlorine and Chlorine Compounds" in *Disinfection, Sterilization, and Preservation* 4th Ed.. S.S. Block. ed.. pp. 137-138 and 149-151. (Philadelphia. PA. Lea & Febiger, 1991).
H. Farkas-Himsley, "Killing of Chlorine-Resistant Bacteria by Chlorine-Bromine Solutions," Applied Microbiology (1964) 12: 1-6.
P.W. Kabler, "Relative Resistance of Coliform Organisms and Enteric Pathogens in the Disinfection of Water with Chlorine," J. American Water Works Association (1951) 43: 553-560.
"*Legionella* 2003: An Update and Statement by the Association of Water Technologies (AWT)," (McLean, VA: Association of Water Technologies, 2003). pp. 1-33.
"Control of *Legionella* in Cooling Towers: Summary Guidelines," (Madison, WI: Wisconsin Division of Health, Aug. 1987), 28 pages.
"Chlorination," Betz Handbook of Industrial Water Conditioning, Seventh Edition, pp. 24-29 (Trevose, PA: Betz Laboratories, Inc., 1976).
"Minimizing the Risk of Legionellosis Associated with Building Water Systems," ASHRAE Guideline Dec. 2000 (Atlanta, GA: ASHRAE, 2000) 19 pages.
A. Smith, et al., "Bromine vs. Gaseous Chlorine: A Comprehensive Review of Case Histories," paper 637 (Corrosion 93, NACE Annual Conference and Corrosion Show, 1993), pp. 637/1-637/12.
A.E. Gillam and R.A. Morton, "The Absorption Spectra of Halogens and Inter-Halogen Compounds in Solution in Carbon Tetrachloride," Proceedings of the Royal Society (London) (1929) vol. 124: 604-616.
J.K. Johannesson, "*The Bromination of Swimming Pools*," American Journal of Public Health (1960) 50: 1731-1736.
J.D. Johnson and W. Sun, "*Bromine Disinfection of Wastewater*," in "Disinfection-Water and Wastewater," J.D. Johnson, ed., pp. 179-191 (Ann Arbor, MI: Ann Arbor Science, 1975).
J.K Johannesson, "*Anomalous Bactericidal Action of Bromamine*," Nature (1958) 181: 1799-1800.
J.C. Albright, "Liquid Bromine Removes Obstinate Algae from 10,000 gpm Tower for $2.10/Day," Petroleum Processing (1948) 3: 421-422.
Y. Kott, "Effect of Halogens on Algae-III. Field Experiment," Water Research (1969) 3: 265-271.
N. Betzer and Y. Kott, "Effect of Halogens on Algae-II. *Cladophora* sp.," Water Research (1969) 3: 257-264. 13 pages.
Y. Kott and J. Edlis, "Effect of Halogens on Algae-I. *Chlorella Sorokiniana* ," Water Research (1969) 3: 251-256.
P.J. Sullivan and B. J. Hepburn, "*The Evolution of Phosphonate Technology for Corrosion Inhibition*," paper 496 (Houston, TX: NACE International, 1995) pp. 496/01-496/13.
A.T. Palin, "The Determination of Free and Combined Chlorine in Water by the Use of Diethyl-p-phenylene diamine," Journal of the American Water Works Association (1957) 49: 873-880.
C.W. Kruse, et al., "*Halogen Action on Bacteria, Viruses, and Protozoa*," in Proc. Natl. Specialty Conference on Disinfection, pp. 113-136 (New York, NY: ASCE, 1970).
R. Aull and T. Krell, "*Design Features and their Affect on High Performance Fill*," paper TP00-01 (Houston, TX: Cooling Technology Institute, 2000) pp. 1-31.
S. Barratt and C.P. Stein, "On Bromine Chloride," Proceedings of the Royal Society (London) (1929) vol. 122: 582-588.
J.F. Mills, "*Interhalogens and Halogen Mixtures as Disinfectants*," in Disinfection-Water and Wastewater, J.D. Johnson ed. pp. 113-143 (Ann Arbor, MI: Ann Arbor Science, 1975).
E.C. Wackenhuth and G. Levine, "*An Investigation of Bromine Chloride as a Biocide in Condenser Cooling Water*," (Pittsburgh, PA: Engineer's Society of Western Pennsylvania, 1974), pp. 1-14.
L.H. Bonaers. T.P. O'Connor and D.T. Burton. "*Bromine Chloride—An Alternative to Chlorine for Fouling Control in Condenser Cooling Systems*," report No. EPA-600/7-77-053 (research Triangle Park, NC: EPA Office of Research and Development, May 1977), 4 pages.

B.H. Keswick, "Bromine-Chloride as an Alternative Disinfectant to Chlorine of Human Enteric Viruses and Other Pathogens in Water and Wastewater", Doctoral Dissertation, University of Hawaii (Ann Arbor, MI: University Microfilms International, 1979), 16 pages.

R.M. Moore, et al., "*Use of a New Bromine-Based Biocide in a Medium-Sized Cooling Tower*," paper IWC-97-51 (Pittsburgh, PA: Engineers' Society of Western Pennsylvania, 1997), 6 pages.

G.D. Nelson, "*Chloramines and Bromamines*," in Kirk Othmer Encyclopedia of Chemical Technology, vol. 5, pp. 565-580 (New York, NY: John Wiley and Sons, 1979).

Z. Zhang and J.V. Matson, "*Organic Halogen Stabilizers: Mechanisms and Disinfection Efficiencies*," paper TP89-05 (Houston, TX: Cooling Tower Institute, 1989), pp. 1-19.

J.C. Peterson, "*Practical Air Washer Treatment in Synthetic Fiber Manufacturing Plants*," paper IWC-87-39 (Pittsburgh, PA: Engineers' Society of Western Pennsylvania, 1987), pp. 366-370.

C. Spurrell and J.S. Clavin, "*Solid Halogen Donor Economically Answers the Challenge of SARA Title III and Corrosion Concerns*," paper 474 (Corrosion.93, NACE Annual Conference and Corrosion Show, 1993), pp. 474/1-474/15.

D.S. Larson, et al., "Improved Microbiological Control Using Halogen Donors in a Pasteurizer," MBAA Technical Quarterly (1993) 30: 173-178.

P. Sweeny, M. Ludensky, and O. Barokhov, "*Mill Performance of a Brominated Methylethylhydantoin Slimicide*," pp. 437-447, Proceedings of the 1999 TAPPI Papermakers Conference (Norcross, GA:: TAPPI, 1999).

F.J. Himpler, P.G. Sweeny, and M. L. Ludensky, "*The Benefits of a Hydantoin-Based Slimicide in Papermaking Applications*," APPITA Journal (Sep. 2001) 54: 427-430.

C.J. Nalepa, et al., "The Control of Bacteria on Surfaces: Effectiveness of Bromine-Based Biocides towards Microbial Biofilms and Biofilm-Associated *Legionella pneumophilia*," paper TP02-13 (Houston, TX: Cooling Technology Institute, 2002), 22 pages.

C.J. Nalepa, et al., The Activity of Oxidizing Biocides towards *Legionella pneumophila* and the Impact of Biofilms on its Control,paper 01278 (Houston, TX: NACE International, 2001, 21 pages.

C.J. Nalepa, et al., "*Case Study: A Comparison of Bromine-Based Biocides in a Medium-Size Cooling Tower*," paper TP98-09 (Houston, TX: Cooling Tower Institute, 1998), 22 pages.

C.J. Nalepa, et al., "*Strategies for Effective Control of Surface-Associated Microorganisms: A Literature Perspective*," IWC-02-01 (Pittsburgh, PA: Engineers' Society of Western Pennsylvania, 2002), 19 pages.

C.J. Nalepa, et al., "Case Study: Minimization of Corrosion Using Activated Sodium Bromide in a Medium-Size Cooling Tower," paper 485 (Corrosion 96 NACE International Annual Conference and Exposition, Houston, TX: NACE International, 1996) 485/1-485/12.

C.J. Nalepa, J.N. Howarth, and R.M. Moore, "*A New Single-Feed Liquid Bromine Biocide for Treatment of Cooling Water*," Presented at the AWT 1999 Annual Convention and Exposition, (McLean, VA: Association of Water Technologies, 1999), 17 pages.

C.J. Nalepa, J.N. Howarth, and F.D. Azamia, "*Factors to Consider When Applying Oxidizing Biocides in the Field*," paper 02223 (Houston, TX: NACE International, 2002), 20 pages.

C. J. Nalepa, H. Ceri, and C.A. Stremick, "*A Novel Technique for Evaluating the Activity of Biocides Against Biofilm Bacteria*," paper 00347 (Corrosion 2000, Houston, TX: NACE International, 2000), pp. 00347/1-00347/19.

C. J. Nalepa, "*New Bromine-Releasing Granules for Microbiological Control of Cooling Water*," paper 03716 (Corrosion 2003 Houston, TX: NACE International, 2003), pp. 03716/1-03716/15.

Cortes CES, et al., "Revisiting the Kinetics and Mechanism of Bromate-Bromide Reaction,"*J. Braz Chem. Soc.*, 12(6): 775-779 (2001).

Current Technology of Chlorine Analysis for Water and Wastewater (Hach Technical Information Series—Booklet No. 17).

E. McCall, J.E. Stout, V.L. Yu, and R. Vidic, "*Efficacy of Biocides against Biofilm-Associated Legionella in a Model System*," paper IWC 99-19 (Pittsburgh, PA: Engineers' Society of Western Pennsylvania, 1999), 7 pages.

Excerpts Fieser and Fieser, Introduction to Organic Chemistry (1957), p. 192.

Excerpts from Loudon, C., *Organic Chemistry* (2nd Edition). Menlo Park, CA: Benjamin/Cummings Publishing Co. (1988), p. A-11.

Affidavit of Shunong Yang, William F. McCoy and Anthony W. Dallmier Under 37 C.F.R. § 1.131 with Exhibit; presumably made public on Sep. 11, 2001, 13-pages.

Attached Appendix B of the Expert Declaration of Gary McKinnie (Mathematical Calculations of Ph Values in Goodenough Examples Prior to Bromine Addition), Moore Exhibit 1019.

F. P. Yu, et al., "*Innovations in Fill Fouling Control*," IWC 00-03 (Pittsburgh, PA: Engineers' Society of Western Pennsylvania, 2000), pp. 26-31.

F.P. Yu, et al., "*Cooling Tower Fill Fouling Control in a Geothermal Power Plant*," paper 529 (Corrosion 98, Houston, TX: NACE International, 1998), p. 529/1-529/11.

Howarth et al., "*First Field Trials of Single-Feed, Liquid Bromine Biocide for Cooling Towers*", Paper TP00-09 (Houston, Tx.: Cooling Technology Institute, Jan. 31-Feb 2, 2000), 17 papes.

Howarth, J.N., et al. "*A New, Bromine-Releasing Solid for Microbiological Control of Cooling Water*", IWC-01-05, (Pittsburgh, PA: Engineers' Society of Western Pennsylvania, 2001), pp. 1-7.

J.C. Conley, E..H. Puzig, and J.E. Alleman, "*Bromine Chemistry—An Alternative to Dechlorination in Cooling Water and Wastewater Disinfection*," IWC-87-42 (Pittsburgh, PA: Engineers' Society of Western Pennsylvania, 1987). pp. 389-395.

J.W. Costerton and P.S. Stewart "Battling Biofilms," Scientific American (Jul. 2001) 285: 75-81.

L.. McNamee, "Efficacy of Hypochlorite vs. Hypobromite in the Removal of a *Pseudomonas aeruginosa* Biofilm," summer Intern report (Bozeman, MT: Montana State University, Center for Biofilm Engineering, 2000). pp. 1-23.

*Guidelines for the Control of Legionnaires' Disease*, (Melbourne, Australia: Health Department Victoria, 1989, (reprinted in 1999), 9 pages.

M. Enzien and B. Yang, "*On-line Performance Monitoring of Treatment Programs for MIC Control*," paper 01279 (Corrosion 2001, Houston, TX: NACE International 2001), 13 pages.

M. Lewin and M. Avarahami, "*The Decomposition of Hypochlorite-Hypobromite Mixtures in the pH Range 7-10*," Journal of the American Chemical Society, (1955) 77: 4491-4498.

M.L. Ludyanskiy and F.J. Himpler, "*The Effect of Halogenated Hydantoins on Biofilms*," paper 405 (Corrrosion 97, Houston, TX: NACE International, 1997) pp. 405/1-405/11.

M.R. Freije, "*Legionellae Control in Health Care Facilities: A Guide for Minimizing Risk*," (Indianapolis, IN: HC Information Resources, Inc. 1996, pp. 25-41.

Principles of Modern Chemistry (1986), D.W. Oxtoby et al.. New York: Saunders college Publishing, pp. 4-7.

Quantitative Chemical Analysis, 3rd ed., D.C. Harris (1991). New York: W.H. Freeman & Co., pp. 181, 195-197.

R. Elsmore, "Development of Bromine Chemistry in Controlling Microbial Growth in Water Systems," International Biodeterioration and Biodegradation (1994) 245-253.

R.M. Moore. W.C. Lotz, and V.R. Perry. "*Activated Sodium Bromide-Artificial Marsh Treatment: A Successful Plant-Wide Program*," paper IWC-95-61 (Pittsburgh, PA: Engineers' Society of Western Pennsylvania, 1995). 12 pgs.

Regulatory Advisory, Waterbome Pathogens—Compliance with Joint Commission on Accrediation of Healthcare Organizations Requirements, web address www.ashe.org/media/water.html, visited Jun. 12, 2002, 9 pages.

W.F. McCoy, et al., "Strategies Used in Nature for Microbial Fouling Control: Applications for Industrial Water Treatment," paper 520 (Houston, TX: NACE International, 1998).

W.G. Characklis and K.C. Marshall, ed., *Biofilms: A Basis for an Interdisciplinary Approach*, (New York, NY: John Wiley & Sons, 1987) p. 3-5.

W.M. Thomas, J. Eccles, and C. Frisker, "*Laboratory Observations of Biocide Efficiency against Legionella in Model Cooling Tower Systems*," paper SE-99-3-4 (Atlanta, GA: ASHRAE Transactions, 1999), pp. 1-17.

Z. Zhang "Disinfection Efficiency and Mechanisms of 1-Bromo-3-Chloro-5,5-Dimethylhydantoin," Doctoral Dissertation, University of Houston, May 1988 pp. 160, 162, 163.

T.C. Kuechler, A Towerbrom® Progress Report, (McLean, VA: Association of Water Technologies, 1993), pp. 1-15.

T.C. Kuechler, et al., "Development of Monsanto's Towerbrom® Microbiocide, a New Bromine Microbiocide for Recirculating Water Systems," (McLean, VA: Association of Water Technologies, 1991), 1991 AWT Conference, p. 1-23.

J.F. Mills, "*The Chemistry of Bromine Chloride in Waste Water Disinfection*," Paper presented to the American Chemical Society Division of Water, Air and Waste Chemicals, Aug. 1973, 20 pages.

Moore's Preliminary Motion No. 1, *Yang v. Moore*, Interference No. 105,230.

Moore's Preliminary Motion No. 2, *Yang v. Moore*, Interference No. 105,230.

Moore Preliminary Motion 3, *Yang v. Moore*, Interference No. 105,230.

Moore Preliminary Motion 4, *Yang v: Moore*, Interference No. 105,230.

Moore Preliminary Motion 5, *Yang v. Moore*, Interference No. 105,230.

Moore's Preliminary Motion 6, *Yang v. Moore*, Interference No. 105,230.

Moore Opposition 1 (Prelim Motion 1), *Yang v. Moore*, Interference No. 105,230.

Yang Alternative Preliminary Motion 1 to Substitute Count, *Yang v. Moore*, Interference No. 105,230.

Yang Miscellaneous Motion 1 to Vacate Interference No. 105,230 in Favor of Interference No. 105,222, *Yang v. Moore*, Interference No. 105,230.

Moore Opposition 1 (Miscellaneous Motion 1), *Yang v. Moore*, Interference No. 105,230.

Yang Opposition to Moore's Preliminary Motion 1, *Yang v. Moore*, Interference No. 105,230.

Yang Opposition to Moore's Preliminary Motion 2, *Yang v. Moore*, Interference No. 105,230.

Yang Opposition 3, *Yang v. Moore*, Interference No. 105;230.

Yang Opposition 4, *Yang v. Moore*, Interference No. 105,230.

Yang Opposition 5, *Yang v. Moore*, Interference No. 105,230.

Moore Reply 1, *Yang v. Moore*, Interference No. 105,230.

Moore Reply 2, *Yang v. Moore*, Interference No. 105,230.

Moore Reply 3, *Yang v. Moore*, Interference No. 105,230.

Moore Reply 4, *Yang v. Moore*, Interference No. 105,230.

Moore Reply 5, *Yang v. Moore*, Interference No. 105,230.

Yang Reply 1 to Moore's Opposition 1, *Yang v. Moore*, Interference No. 105,230.

Yang Reply 1, *Yang v. Moore*, Interference No. 105,230.

Moore Request for Rehearing of the Decision on Moore Preliminary Motion 2, *Yang v. Moore*, Interference No. 105,230.

Decision—Rehearing—Bd. R. 125(c) (Including Recommendation to Examiner—Bd. R. 127(c)), *Yang v. Moore*, Interference No. 105,230.

Judgment—Bd. R. 127, Sep. 29, 2005, *Yang v. Moore*, Interference No. 105,230.

Moore Request for Rehearing of the Judgment, *Yang v. Moore*, Interference No. 105,230.

Decision—Interlocutory Motions, *Yang v. Moore*, Interference No. 105,230.

Decision on Moore Preliminary Motions 2 and 3, *Yang v. Moore*, Interference No. 105,230.

Summary of Decisions on Miscellaneous and Preliminary Motions, *Yang v. Moore*, Interfence No. 105,230.

Moore Preliminary Motion 1, *Yang v. Moore*, Interference No. 105,223.

Moore Preliminary Motion 2, *Yang v. Moore*, Interference No. 105,223.

Moore Preliminary Motion 3, *Yang v. Moore*, Interference No. 105,223.

Decision—Rehearing—Bd. R. 125(c) (Including Recommendation to Examiner—Bd. R. 127(c)), *Yang v. Moore*, Interference No. 105,223.

Moore Request for Rehearing of the Judgment, *Yang v. Moore*, Interference No. 105,223.

Judgment—Bd. R. 127, Sep. 29, 2005, *Yang v. Moore*, Interference No. 105,223.

Moore Request for Rehearing of the Decision on Moore Preliminary Motion 3, *Yang v. Moore*, Interference No. 105,223.

Moore Exhibit 1106 (Amendment under 37 C.F.R.§ 1.607, U.S. Appl. No. 09/451,319), *Yang v. Moore*, Interference 105,222, 105,223, and 105,230.

Moore Exhibit 1107 (Moore's Clean Copy of Claims), *Yang v. Moore*, Interference 105,222, 105,223, and 105,230.

Decision—Interlocutory Motions (Bd. R. 125(b)), Sep. 13, 2005, *Yang v. Moore*, Interference No. 105,223.

Summary of Decisions on Miscellaneous and Preliminary Motions, *Yang v. Moore*, Interfence No. 105,223.

Moore Reply 1, *Yang v. Moore*, Interference No. 105,223.

Moore Reply 2, *Yang v. Moore*, Interference No. 105,223.

Moore Reply 3, *Yang v. Moore*, Interference No. 105,223.

Yang Opposition 1, *Yang v. Moore*, Interference No. 105,223.

Yang Opposition 2, *Yang v. Moore*, Interference No. 105,223.

Yang Opposition 3, *Yang v. Moore*, Interference No. 105,223.

Moore Opposition 1 (Prelim. Motion 1), *Yang v. Moore*, Interference No. 105,223.

Moore Opposition 1 (Misc. Motion 1), *Yang v. Moore*, Interference No. 105,223.

Yang Alternative Preliminary Motion 1 to Designate Claims as not Corresponding to Count 1, *Yang v. Moore*, Interference No. 105,223.

Yang Miscellaneous Motion 1 to Vacate Interference No. 105,223 in Favor of Interference No. 105,222, *Yang v. Moore*, Interference No. 105,223.

Yang Reply 1 to Moore Opposition 1 (Misc. Motion 1), *Yang v. Moore*, Interference No. 105,223.

Decision on Moore Preliminary Motion 3, *Yang v. Moore*, Interference Nb. 105,223.

Yang Reply 1 to Moore Opposition 1 (Prelim. Motion 1), *Yang v. Moore*, Interference No. 105,223.

Moore Preliminary Motion 1, *Yang v. Moore*, Interference No. 105,222.

Moore's Preliminary Motion No. 2, *Yang v. Moore*, Interference No. 105,222.

Moore Preliminary Motion 3, *Yang v. Moore*, Interference No. 105,222.

Moore Preliminary Motion 4, *Yang v. Moore*, Interference No. 105,222.

Moore Preliminary Motion 5, *Yang v. Moore*, Interference No. 105,222.

Yang Opposition 1, *Yang v. Moore*, Interference No. 105,222.

Yang Opposition to Moore's Preliminary Motion 2, *Yang v. Moore*, Interference No. 105,222.

Yang Opposition 3, *Yang v. Moore*, Interference No. 105,222.

Yang Opposition to Moore's Preliminary Motion 4, *Yang v. Moore*, Interference No. 105,222.

Yang Opposition 5, *Yang v. Moore*,Interference No. 105,222.

Yang Opposition 6, *Yang v. Moore*; Interference No. 105,222.

Yang Miscellaneous Motion 1 to Add Patent Nos. 6,156,229, 6,287,473, 6,123,870 and U.S. Appl. No. 09/785,890 to Interference, *Yang v. Moore*, Interference No. 105,222.

Yang Alternative Preliminary Motion 2 to Substitute Count, *Yang v. Moore*, Interference No. 105,222.

Yang Reply 1 (Misc. Motion 1), *Yang v. Moore*, Interference No. 105,222.

Moore Opposition 1 (Prelim. Motion 1), *Yang v. Moore*, Interference No. 105,222.

Moore Opposition 1 (Misc. Motion 1), *Yang v. Moore*, Interference No. 105,222.

Moore Opposition 2, *Yang v. Moore*, Interference No. 105,222.

Moore Responsive Motion 6, *Yang v. Moore*, Interference No. 105,222.

Judgment—Bd. R. 127, Sep. 29, 2005, *Yang v. Moore*, Interference No. 105,222.

Yang Reply 2, *Yang v. Moore*, Interference No. 105,222.

Yang Reply 1 to Moore's Opposition 1, *Yang v. Moore*, Interference No. 105,222.

Yang Preliminary Motion 1 to Designate Claims as not Corresponding to the Count, *Yang v. Moore*, Interference No. 105,222.
Moore Reply 1, *Yang v. Moore*, Interference No. 105,222.
Moore Reply 2, *Yang v. Moore*, Interference No: 105,222.
Moore Reply 3, *Yang v. Moore*, Interference No. 105,222.
Moore Reply 4, *Yang v. Moore*, Interference No. 105,222.
Moore Reply 5, *Yang v. Moore*, Interference No. 105,222.
Moore Reply 6, *Yang v. Moore*, Interference No. 105,222.
Decision—Interlocutory Motions (Bd. R.125(b)), *Yang v. Moore*, Interference No. 105,222.
Summary of Decisions on Miscellaneous and Preliminary Motions, *Yang v. Moore*, Interference No. 105,222.
Decision on Moore Preliminary Motions 2 and 3, *Yang v. Moore*, Interference No. 105,222.
Willard et al., *"Elementary Quantitative Analysis"*, Third Edition, Chapter XIV, 1933, pp. 261-271.
B.S. Ault et al., "Infrared and Raman Spectra of the $M^+Cl_3^-$ Ion Pairs and Their Chlorine-Bromine Counterparts Isolated in Argon Matrices", Journal of Chemical Physics, 1976, vol. 64, No. 12, pp. 4853-4859.
A.A. Frost, et al. "Kinetics and Mechanism: A Study of Homogeneous Chemical Reactions", 1953, p. 23.
"Evolution of Industrial Water Treatment," Betz Handbook of Industrial Water Conditioning, Seventh Edition, pp. 7-15 (Trevose, PA: Betz Laboratories, Inc. 1976).
Ainstein, V.G. "The General Course of Processes and Apparatuses of Chemical Technology," The Second Book, 2002, pp. 1224-1225.
Ainstein, V.G. "The General Course of Processes and Apparatuses of Chemical Technology," The Second Book, 2002, pp. 1307-1309.
Farkas and Lewin; "The Dissociation Constant of Hypobromous Acid"; J. Am. Chem. Soc.; 1950; 72; 5766-5767.
"Halogens as Oxidizing Agents"; http://www.chemguide.co.uk/inorganic/group7/halogensasoas.html; accessed on Dec. 8, 2008; 8 pages.
Odeh, ILhab N. et al.; "Kinetics and Mechanisms of Bromine Chloride Reactions with Bromite and Chlorite Ions"; Inorg. Chem.; 2004; 43; 7412-7420.
Tellinghuisen, Joel; "Precise Equilibrium Constants From Spectrophotometric Data: BrCl in Br2/Cl2 Gas Mixtures"; J. Phys. Chem. A; 2003; 107; 753-757.
Urtz, Bruce; "Combined Halogens: New Products to Combat an Old Problem" Solutions!, Online Exclusives, Mar. 2003; http://www.tappi.org/Bookstore/Technical-Papers/Journal-Articles/Archive/Solutions/Archives/2003/March/Combined-halogens-new-products-to-combat-an-old-problem-Solutions-Online-Exclusives-March-2003.aspx; accessed on Jul. 20, 2011; 6 pages.
Wang, Tian Xiang et al.; "Equilibrium, Kinetic, and UV-Spectral Characteristics of Aqueous Bromine Chloride, Bromine, and Chlorine Species"; Inorg. Chem.; 1994; 33, 5872-5878.
"Bromine Chloride for Treating Cooling Water and Wastewater", brochure CD 6-76; Ethyl Corporation, Commercial Development Division; Ferndale, Michigan; 1976; 10 pages.
Keister et al.; ""Stabilized" Bromine Biocides: Definitions, Chemistry, and Performance", AWT Annual Convention, McLean, VA 2002; 7 pages.

\* cited by examiner

US 8,409,630 B2

CONTINUOUS PROCESSES FOR PREPARING CONCENTRATED AQUEOUS LIQUID BIOCIDAL COMPOSITIONS

REFERENCE TO RELATED APPLICATIONS

This application is a continuation of application Ser. No. 09/451,344, filed Nov. 30, 1999, now issued as U.S. Pat. No. 6,352,725, which is a continuation-in-part of commonly-owned application Ser. No. 09/442,025, filed Nov. 17, 1999, now issued as U.S. Pat. No. 6,306,441, which in turn is a continuation-in-part of commonly-owned Continued Prosecution Application (CPA) No. 09/088,300, now issued as U.S. Pat. No. 6,068,861, which continues the prosecution of prior commonly-owned application Ser. No. 09/088,300, filed Jun. 1, 1998.

BACKGROUND

Bromine-based biocides have proven biocidal advantages over chlorination-dechlorination for the microbiological control of cooling waters and disinfection of waste treatment systems. The water treatment industry recognizes these advantages to be cost-effective control at higher pH values, almost no loss in biocidal activity in the presence of ammonia, and effective control of bacteria, algae and mollusks.

A common way of introducing bromine based biocides into a water system is through the use of aqueous NaBr in conjunction with NaOCl bleach. The user feeds both materials to a common point whereupon the NaOCl oxidizes the bromide ion to $HOBr/OBr^-$. This activated solution is then introduced directly into the water system to be treated. The feeding of the two liquids in this fashion is necessary because the $HOBr/OBr^-$ mixture is unstable and has to be generated on-site just prior to its introduction to the water. Furthermore, the feeding, and metering of two liquids is cumbersome, especially as the system has to be designed to allow time for the activation of bromide ion to occur. Consequently many biocide users have expressed the need for a single-feed, bromine-based biocide. Molecular bromine chloride is deemed to meet these demands. It is a liquid at room temperature and can be fed directly to the water system, where immediate hydrolysis occurs to yield HOBr.

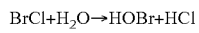

$BrCl + H_2O \rightarrow HOBr + HCl$

Bromine chloride is a fuming, red liquid or gas, with a boiling point of 5° C., and a vapor pressure of 1800 mm at 25° C. It corrodes most metals in the presence of water.

It can be seen that certain characteristics of bromine chloride—especially its corrosiveness, high vapor pressure and fuming tendencies—necessitate care and skill in its handling and use.

An economically acceptable way of stabilizing high concentrations of aqueous solutions of bromine chloride is described in U.S. Pat. No. 5,141,652 to Moore, et al. The solution is prepared from bromine chloride, water and a halide salt or hydrohalic acid. These solutions were found to decompose at a rate of less than 30% per year and in cases of high halide salt concentration, less than 5% per year. Moreover, solutions containing the equivalent of 15% elemental bromine could be prepared. Unfortunately, the relatively high acidity of these solutions and their tendency to be corrosive and fuming impose limitations on their commercial acceptance.

The commonly-owned copending continued prosecution application now issued as U.S. Pat. No. 6,068,861, referred to at the outset describes, inter alia, a new process of forming concentrated aqueous solutions of biocidally active bromine and in so doing, provides novel and eminently useful concentrated aqueous biocidal solutions formed from bromine chloride. Such solutions are formed by a process which comprises mixing (a) bromine chloride with (b) an aqueous solution of alkali metal salt of sulfamic acid (preferably the sodium salt), the resulting solution having a pH of at least about 7, e.g., in the range of 7 to about 14, and preferably above 7 to about 14. Most preferably the pH is in the range of about 13.0 to about 13.7. The amounts of (a) and (b) used are such that (i) the content of active bromine in the solution is at least 100,000 ppm (wt/wt) and (ii) the atom ratio of nitrogen to active bromine from (a) and (b) is greater than 0.93, and preferably is greater than 1.

The commonly-owned copending application referred to at the outset of which the present application is a continuation-in-part describes, inter alia, a process of producing a concentrated liquid biocide composition by a process which comprises (A) continuously feeding into mixing apparatus (i) bromine chloride and (ii) an aqueous solution of alkali metal salt of sulfamic acid (preferably a sodium salt of sulfamic acid), proportioned to produce an aqueous product having an active bromine content of at least 100,000 ppm (wt/wt), and an atom ratio of nitrogen to active bromine from (i) and (ii) greater than 0.93 (preferably greater than 1), and (B) withdrawing such product from the mixing apparatus at a rate sufficient to enable the continuous feeding in A) to be maintained. In certain embodiments of the process, the bromine chloride is continuously formed from equimolar amounts of bromine and chlorine, and at least a portion of the bromine chloride being continuously produced is used as the continuous feed of bromine chloride in step A) above. Thus in plant facilities where bromine chloride is required or desired for use(s) in addition to that required to maintain the continuous feed of (i) in step A) above, the continuous production of the bromine chloride can be scaled up to serve all such uses. A preferred embodiment of the process includes, in addition to steps A) and B) as described above, the following concurrent operation, namely, continuously, but alternately, withdrawing from at least one and then from at least one other of at least two reaction vessels, an aqueous solution of alkali metal salt of sulfamic acid at a rate that maintains the stream of (ii) in A), and during the time the solution is being withdrawn from said at least one of at least two reaction vessels, forming additional aqueous solution of alkali metal salt of sulfamic acid in at least one other of at least two reaction vessels from which solution is not then being withdrawn. In this way, aqueous alkali metal sulfamate solution can be continuously withdrawn from one or more tanks ("Tank(s) I") to serve as the continuous feed of (ii) in A), while forming more of such solution in one or more other tanks ("Tank(s) II"), so that when Tank(s) I is/are depleted, the system is switched to Tank(s) II which then serve(s) as the supply for the continuous feed of (ii) in A) until depleted, and by that time more of such solution has been formed in Tank(s) I. Thus by alternating the supply and the production from one tank (or group of tanks) to another tank (or group of tanks) and switching back and forth between the filled tanks as the supply, the continuous feed of the aqueous alkali metal sulfamate solution can be maintained without material interruption.

SUMMARY OF THE INVENTION

One objective of this invention is to enable a process of the last-mentioned commonly-owned copending application wherein at least a portion of the bromine chloride is being continuously produced and used as one of the continuous feeds, to be carried out not only in a commercially-feasible, highly efficient manner on a continuous basis, but in addition, to include efficient automatic continuous process control in such process. Other objectives may appear hereinafter.

In one of its embodiments this invention provides a process of producing a concentrated liquid biocide composition which process comprises:
a) continuously forming bromine chloride from separate feed streams of bromine and chlorine by maintaining said streams under automatic feed rate control whereby the streams are continuously proportioned to come together in equimolar amounts to form bromine chloride;
b) continuously forming an aqueous product having an active bromine content of at least 100,000 ppm (wt/wt), a pH of at least 7, and an atom ratio of nitrogen to active bromine greater than 0.93:1 by feeding into mixing apparatus separate fee streams of (i) bromine chloride formed in a) and (ii) an aqueous solution of alkali metal salt of sulfamic acid, under automatic feed rate control whereby the feed streams are continuously proportioned to come together in amounts that produce an aqueous product having an active bromine content of at least 100,000 ppm (wt/wt), a pH of at least 7, and an atom ratio of nitrogen to active bromine from (i) and (ii) greater than 0.93:1; and
c) withdrawing said aqueous product from said mixing apparatus at a rate sufficient to enable the continuous feeding in a) and b) to be maintained.
Preferably the automatic feed rate controls in a) and b) are under nested cascade ratio flow control.

Since the reaction between the bromine chloride and the alkali metal sulfamate solution is exothermic, it is desirable to control the temperature of this reaction so that the temperature of the aqueous product being formed does not exceed about 50° C., and preferably is in the range of about 25 to about 40° C., and most preferably is maintained at about 30° C. Such control may be accomplished, for example, by promptly passing the effluent from the mixing apparatus through a proximately-disposed heat exchanger to remove excess heat from the effluent. Another way of accomplishing such temperature control is to suitably precool the aqueous alkali metal sulfamate solution before it reaches the mixing device such that the temperature of the effluent stays within the foregoing temperature conditions. Both such methods of temperature control can be utilized, if desired.

Another embodiment of the above process includes, in addition to steps a), b), and c) as described above, forming, either periodically or continuously, the aqueous alkali metal sulfamate solution by reaction between sulfamic acid and alkali metal base such as alkali metal hydroxide in water.

One preferred embodiment of the above processes includes the following concurrent operation, namely, continuously, but alternately, withdrawing from at least one and then from at least one other of at least two reaction vessels, an aqueous solution of alkali metal salt of sulfamic acid at a rate that maintains the stream of (ii) in b), and during the time the solution is being withdrawn from at least one of at least two such reaction vessels, forming additional aqueous solution of alkali metal salt of sulfamic acid in at least one other of such reaction vessels from which solution is not then being withdrawn. In this way, aqueous alkali metal sulfamate solution can be continuously withdrawn from one or more tanks ("Tank(s) I") to serve as the continuous feed of (ii) in b), while forming more of such solution in one or more other tanks ("Tank(s) II"), so that when Tank(s) I is/are depleted, the system is switched to Tank(s) II which then serve(s) as the supply for the continuous feed of (ii) in A) until depleted, and by that time more of such solution has been formed in Tank(s) I. Thus by alternating the supply and the production from one tank (or group of tanks) to another tank (or group of tanks) and switching back and forth between the filled tanks as the supply, the continuous feed of the aqueous alkali metal sulfamate solution can be maintained without material interruption.

Another preferred embodiment of the above processes includes the following concurrent operation, namely, continuously withdrawing an aqueous solution of alkali metal salt of sulfamic acid from a circulating inventory of alkali metal salt of sulfamic acid, the withdrawal being at a rate that maintains the stream of (ii) in b), and continuously replenishing the circulating inventory from a supply of such aqueous solution of alkali metal salt of sulfamic acid from a reaction vessel in which aqueous solution of alkali metal salt of sulfamic acid is produced at least periodically in quantity sufficient to at least maintain such circulating inventory. By maintaining a circulating inventory of the aqueous solution of alkali metal salt of sulfamic acid in a pump around circulation loop, only one reaction vessel is required for forming such solution from sulfamic acid, an alkali metal base such as alkali metal hydroxide, and water.

The above and other embodiments and features of this invention will be still further apparent from the ensuing description, the accompanying drawings, and/or the appended claims.

FURTHER DETAILED DESCRIPTION OF THE INVENTION

Figure 1:
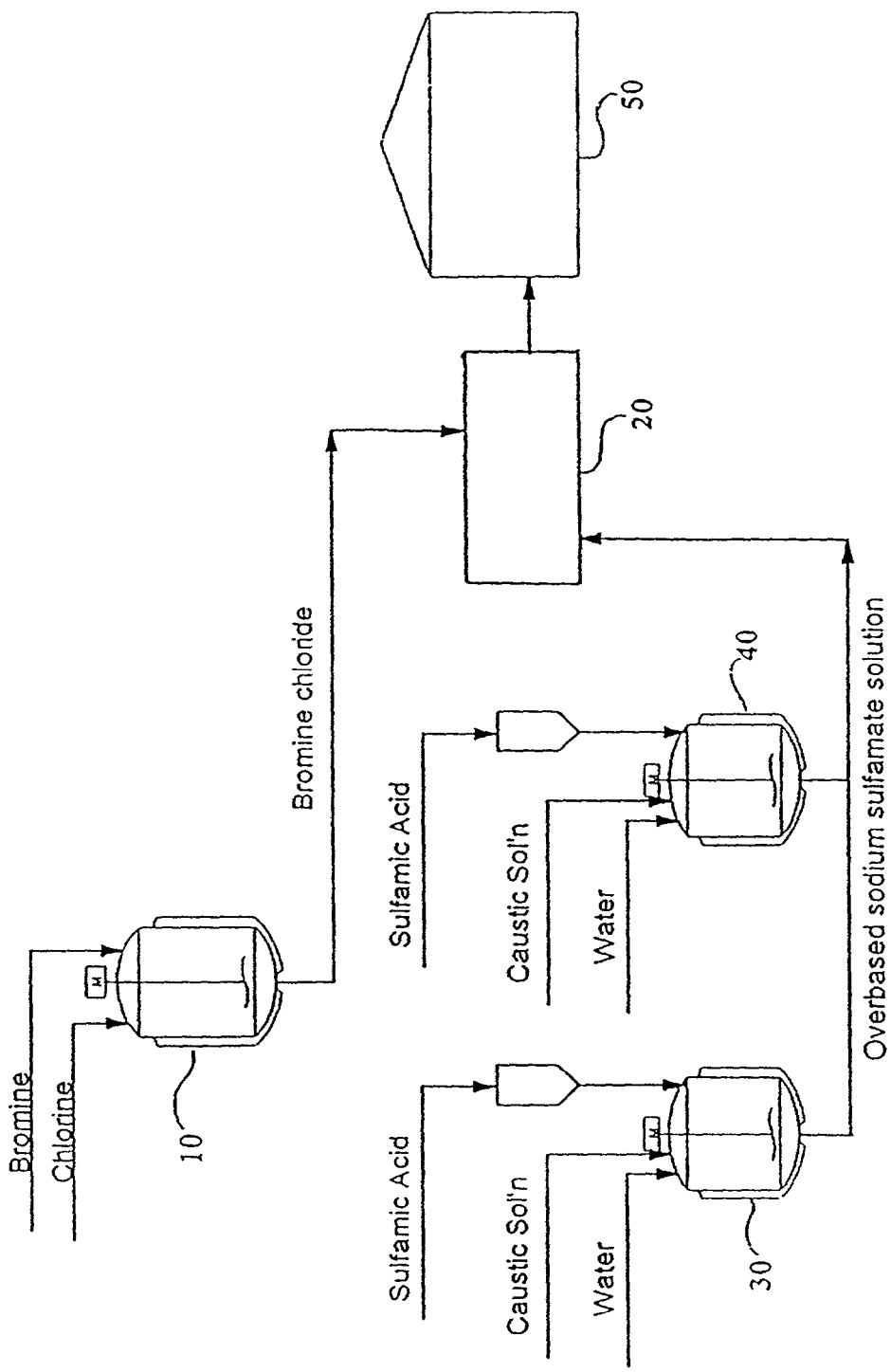
FIG. 1 is a schematic flow diagram of a plant layout suitable for the practice of a continuous processes.

Various types of mixing apparatus can be used in the practice of this invention. In one preferred embodiment the mixing apparatus comprises a static mixer. The static mixer can be of any suitable design and configuration as long as it is capable of continuously receiving the continuous feed streams of bromine chloride and aqueous alkali metal sulfamate solution, and continuously discharging a mixture formed from these feed streams that is substantially uniform in composition and thus satisfies product specifications.

Another preferred mixing apparatus comprises a vessel equipped with a mechanical stirrer. In this case, the vessel continuously receives the continuous feed streams of bromine chloride and aqueous alkali metal sulfamate solution, and either continuously or intermittently discharges a substantially uniform mixture formed from these feed streams.

When introducing the bromine chloride or bromine into the aqueous solution of alkali metal salt of sulfamic acid, it is desirable to maintain the desired pH of the resulting solution at 7 or above by also introducing into the solution (continuously or intermittently, as desired) additional alkali metal base, such as by a co-feed of an aqueous solution of alkali metal base.

The mechanical stirrer can be programmed to operate continuously or intermittently as long as the discharge from the vessel is constantly substantially uniform in composition. Thus if the discharge from the vessel is intermittent, the incoming continuous feeds are preferably agitated during at least most of the time the vessel is filling up to a predetermined volume at which point the contents of the vessel are discharged more rapidly than the total incoming feeds until the vessel reaches a predetermined low volume, at which point the discharge is discontinued so that the vessel begins to fill up again. On the other hand, if the discharge is continuous, the system is designed and constructed such that the total incoming volume to the vessel and the concurrent outgoing volume from the vessel remain equal and so that the vessel continuously contains a predetermined volume of contents which are being mixed by the mechanical stirrer. In such case, the stirrer preferably is operated continuously.

The bromine chloride can be preformed bromine chloride maintained and sourced from storage tanks. Preferably however the bromine chloride is concurrently being prepared in a suitable corrosion-resistant reaction vessel on a continuous basis from equimolar amounts of bromine and chlorine. As indicated above, the amount of bromine chloride being continuously produced can equal the amount of bromine chloride being continuously fed to the mixing apparatus, when there is no other need or desire for additional amounts of bromine chloride. But if there are other such needs or desires, the amount of bromine chloride production can be scaled up to meet such needs or desires. The bromine chloride is typically formed by contacting the reactants in equimolar quantities and maintaining the temperature of the mixture in the range of about 10 to about 50° C.

Use of bromine chloride as the source of the active bromine in the concentrated stabilized liquid biocide formulations produced pursuant to this invention is highly advantageous. When such biocidal formulations are used to treat water, all of the bromine of the bromine chloride is made available as active bromine in the resulting highly dilute solution. In other words, the chlorine of the bromine chloride is converted in the process to dissolved alkali metal chloride salt, thereby liberating the bromine as the active bromine content of the biocidal composition. Thus the more expensive component of the bromine chloride—viz., bromine—is fully utilized in forming active bromine in the aqueous biocidal composition, and concurrently the less expensive component—the anionic chlorine in the bromine chloride—makes this beneficial result possible.

The aqueous solution of alkali metal salt of sulfamic acid (alkali metal sulfamate) can be preformed and sourced from storage vessels in supplying the other continuous feed to the mixing apparatus. However it is preferred to concurrently produce such aqueous solution at a rate sufficient to at least continuously supply the amount required to maintain such continuous feed to the mixing apparatus. If there are other needs or desires for such aqueous solution, the amount of solution produced can be scaled up to satisfy such needs or desires.

It is possible to form the aqueous solution of alkali metal salt of sulfamic acid by mixing dry sulfamic acid with a dry water-soluble the alkali metal base also in the dry state, and then mix the resultant dry mixture of solids with water. It is also possible to form the aqueous solution of alkali metal salt of sulfamic acid by mixing dry sulfamic acid with an aqueous solution of alkali metal base. However, the aqueous solution of alkali metal sulfamate is preferably formed by mixing together a slurry of sulfamic acid in water and a solution of the water-soluble alkali metal base.

Any water-soluble inorganic alkali metal base can be used in forming the aqueous solution of alkali metal sulfamate. Examples of such bases include the oxides, hydroxides, carbonates, bicarbonates, acetates, sulfates, and the like. While a water-soluble basic salt or oxide of any alkali metal can be used, the sodium salts or oxides are preferred. However potassium salts or oxides are also very useful. Mixtures of two or more water-soluble sodium bases, mixtures of two or more water-soluble potassium bases, or mixtures of one or more water-soluble sodium bases and one or more water-soluble potassium bases can be used. Highly preferred are aqueous sodium hydroxide solutions which can be formed from sodium oxide or sodium hydroxide. Typically the aqueous solution will contain in the range of about 10 to about 55 wt % of the alkali metal base, but any concentration of such base that enables the formation of an aqueous bromine chloride solution meeting the pH requirements of this invention can be employed.

Besides having an active bromine content of at least 100,000 ppm (wt/wt), the concentrated solution emanating from the mixing apparatus preferably has a pH of at least 7, e.g., a pH in the range of 7 to about 14, and preferably above 7 to about 14. Most preferably this solution is a solution with a pH in the range of about 13.0 to about 13.7. The pH of the concentrated solution is typically governed by the pH of the aqueous alkali metal sulfamate solution used as the feed to the mixing apparatus.

It is possible for the solution emanating from the mixing apparatus to have a pH with a numerical value lower than desired, and to feed additional base into the solution after it has left the mixing apparatus to raise the pH to the desired numerical value. Alternatively, a separate aqueous solution of alkali metal base can be fed concurrently and continuously to the mixing apparatus to achieve a more alkaline (basic) concentrated product solution leaving the mixing apparatus. Neither of these latter two procedures is a preferred way to operate, however.

Therefore, in the preferred operating modes the proportions of the bromine chloride and the aqueous alkali metal sulfamate solution continuous feed streams to the mixing apparatus are such that (i) the content of active bromine in the resulting product solution is at least 100,000 ppm (wt/wt) and (ii) the atom ratio of nitrogen to active bromine from these feed streams is greater than 0.93, and more preferably in the range of about 1.0 to about 1.4.

By utilizing bromine chloride with caustic in the stabilized bromine composition, higher levels of active halogen are achievable, compared to the levels obtained by the addition of sodium hypochlorite to sodium bromide. The process and the compositions formed also have about twice the content of active bromine as the most concentrated solutions produced pursuant to Goodenough, et al. U.S. Pat. No. 3,558,503. Moreover, even at the high levels of active bromine that exist in the compositions of this invention, it has been found possible to provide biocidal compositions that maintain these high levels of active bromine for at least a two-month period, and that do not exhibit a visible or offensive vapor or odor during this period.

In each of the embodiments of this invention the operation is preferably conducted such that the concentrated product solution produced in the process has an active bromine content in the range of about 120,000 ppm wt/wt (12 wt %) to about 180,000 ppm wt/wt (18 wt %). Also in each of the embodiments of this invention, the atom ratio of nitrogen to active bromine in the concentrated product solution is preferably at least 1:1, e.g., in the range of about 1.1 to about 1.5. Still higher ratios can be employed, if desired. A particularly preferred atom ratio is from 1.0:1 to 1.4:1.

The processes of this invention are continuous processes and involve continuous feeds to the mixing apparatus. In addition, some embodiments of the invention involve continuous formation of bromine chloride, or continuous contacting of bromine and chlorine to form bromine chloride, or continuous alternate withdrawal of an aqueous solution of alkali metal salt of sulfamic acid from at least one reaction vessel while another quantity of such solution is being formed in at least one other such vessel. In such embodiments the term "continuous" or "continuously" is not meant to exclude interrupted feeds or withdrawals. Generally, if such interruptions occur, they are of short duration and are such as not to materially affect the steady state operation of the overall process, and also are such as not to cause production of a significant quantity of off-specification concentrated product solution. An example of such a slight, non-adverse interruption may occur when switching the flow of aqueous solution of alkali metal salt of sulfamic acid from at least one reaction vessel to another such vessel, an operation which is referred to above as part of a "continuous" feed. As long as such switching operation does not disrupt the operation or result in the formation of a significant quantity of off-specification concentrated product solution, such interruption is acceptable and is within the spirit of the term "continuous". An exception exists where the term "continuous" does not allow for interruption, namely in any case where both continuous and non-continuous (e.g., "intermittent") operation in a given step or operation are both expressly referred to herein. An example of this exception is the embodiment where product is continuously withdrawn from above-referred-to vessel that is equipped with a mechanical stirrer. Such "continuous" withdrawal is not interrupted because in another embodiment expressly referred to herein, the withdrawal of the same product from the same vessel is specifically described as "intermittent". Thus both alternatives (continuous and non-continuous) are expressly referred to in this disclosure.

Reference is now made to the drawings, which are largely self-explanatory.

FIG. 1

In the plant flow diagram schematically depicted in FIG. 1, separate equimolar streams of bromine and chlorine are fed, preferably continuously, into stirred jacketed reactor 10. The contents of reactor 10 are typically maintained at a temperature in the range of about −30 to about 30° C. so that bromine chloride is produced, preferably continuously. The bromine chloride is transmitted continuously into mixing apparatus 20. Concurrently sulfamic acid, a 15-25 wt % aqueous solution of sodium hydroxide, and water are charged into either jacketed reactor 30 or jacketed reactor 40, and the resultant mixture therein is agitated and maintained at about 10 to about 50° C. The sulfamic acid and the sodium hydroxide are proportioned to produce in the reactor an aqueous solution of sodium sulfamate having a pH which preferably is in the range of about 13.0 to about 14.0. The reactor 30 or 40 which is not then being used to prepare such aqueous sodium sulfamate solution, contains an identical aqueous solution previously made therein in the same manner. A stream of such aqueous sodium sulfamate solution is continuously withdrawn from reactor 30 or 40 (as the case may be) which contains the previously made solution, and this stream is continuously fed into mixing apparatus 20. The interaction between the bromine chloride and the sodium sulfamate solution tends to be exothermic. Therefore, it is desirable, particularly in large scale facilities, to cool the mixture as it is being formed. The effluent from mixing apparatus 20 is the concentrated stabilized aqueous biocidal formulation. This product solution is transferred from mixing apparatus 20 to a storage tank 50 or equivalent container such as a railcar or tank truck. If mixing apparatus 20 is a static mixer, the effluent from the static mixer is continuously transferred to the storage tank 50.

On the other hand, if mixing apparatus 20 is, say, a vessel equipped with a mechanical stirrer, and such vessel is intermittently drained so that its contents oscillate between high and low contents of product solution, the transmission of the product solution from such mixing apparatus 20 to storage tank 50 is intermittent. Means (not shown) such as electrically-operated valves and associated electronics for sensing and signaling when to shut one valve while opening the other are included so that the continuous alternate flow of aqueous sodium sulfamate solution from one and then the other of reactors 30 and 40 to mixing apparatus 20 can be maintained on a continuous basis.

Instead of the separate feeds depicted in the drawing of sulfamic acid, a 15-25 wt % aqueous solution of sodium hydroxide, and water that alternate back and forth between one of reactors 30 and 40 while the other reactor is being drained, separate flows of the aqueous solution of sodium hydroxide and a preformed aqueous slurry of sulfamic acid can be fed alternately to these reactors. It may be expected that other variations and details in the depicted schematic plant flow diagram and/or in the mode of operation will now be readily apparent to those of ordinary skill in the art.

Automatic Process Flow Controls

Figure 2:
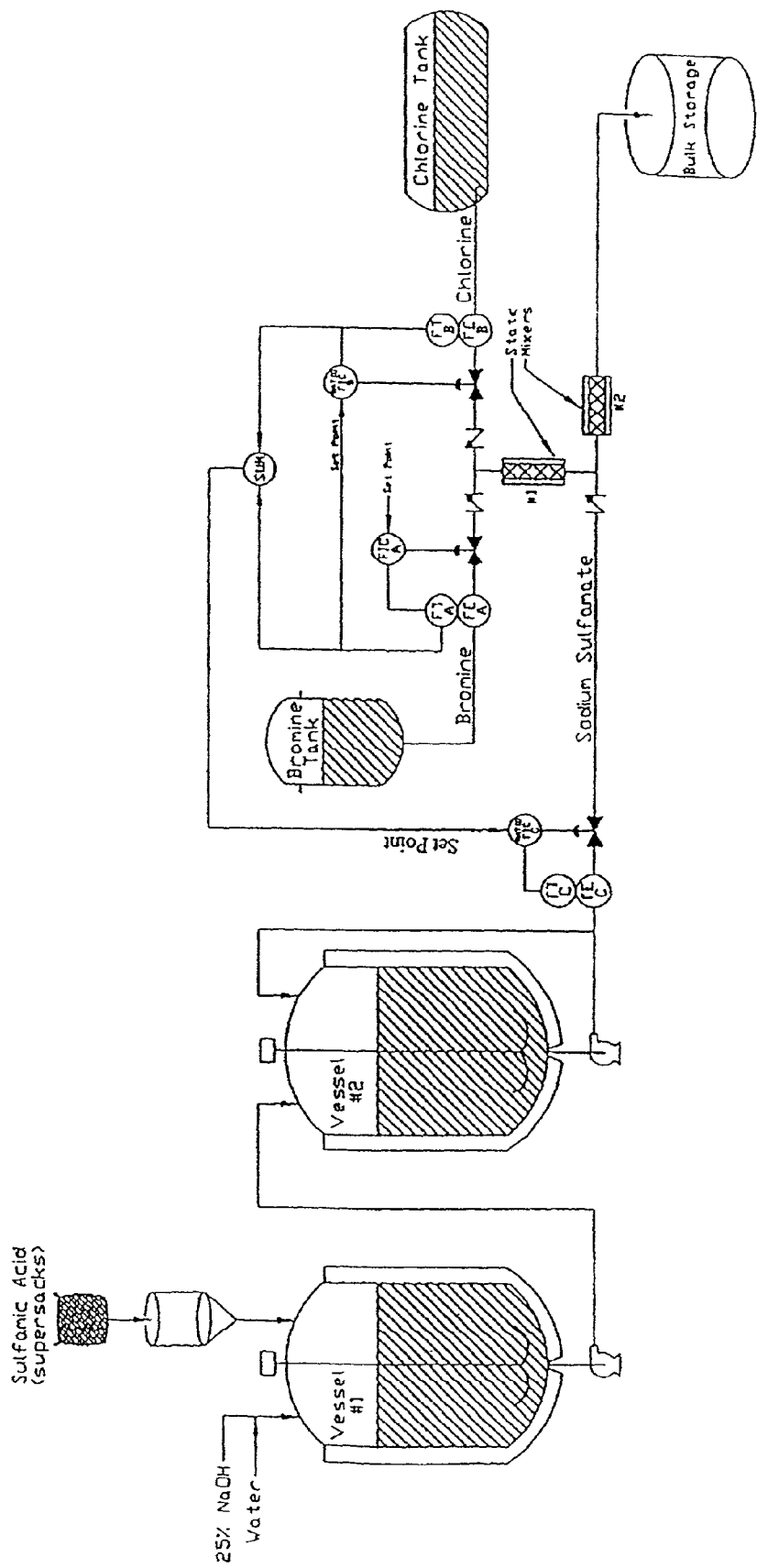
FIG. 2 is a schematic flow diagram of a plant layout of this invention in which an automatic flow control system is included.
Figure 3:
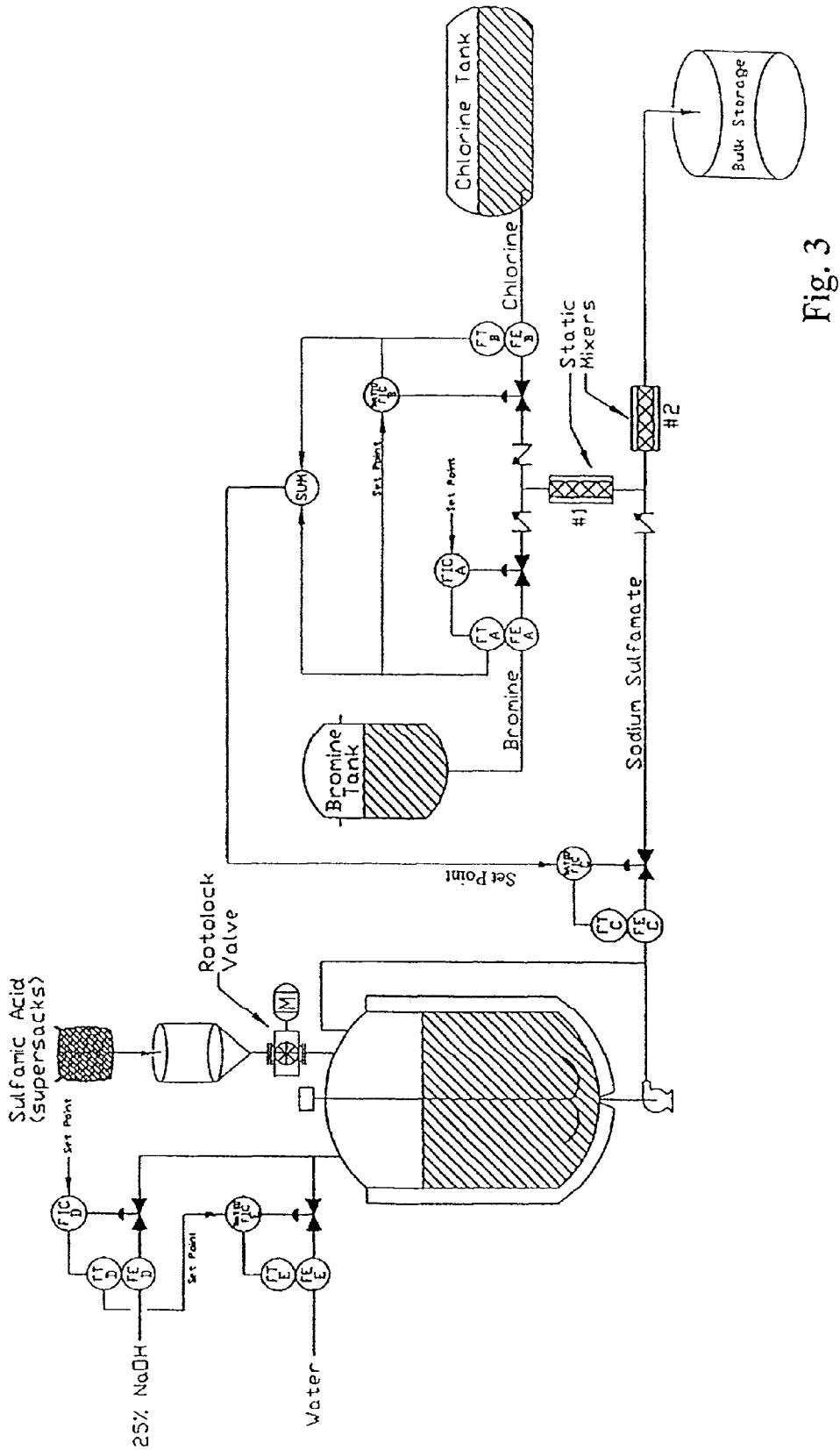
FIG. 3 is a schematic flow diagram of another plant layout of this invention in which an automatic flow control system is included.

In the practice of this invention, the various process embodiments are carried out with automatic process flow controls now to be described. Exemplary flow diagrams involving such automatic process flow controls are schematically depicted in FIGS. 2 and 3. Both such flow diagrams utilize the same method to simultaneously feed bromine, chlorine, and sodium sulfamate. The difference between the two is that FIG. 2 requires two vessels. The first vessel is used to neutralize sulfamic acid to sodium sulfamate. The second vessel is used as a feed tank to continuously feed sodium sulfamate to the rest of the process. The flow diagram of FIG. 3 is a "1-pot" process using a single reactor vessel to continuously neutralize sulfamic acid and feed sodium sulfamate to the rest of the process.

The following process descriptions as regards FIGS. 2 and 3 utilize feedback process control logic. A description of the typical instrumentation elements is provided here to help better understand how this logic process works.

A feedback control loop (for flow control) consists of three elements: (1) a sensor device to measure flow, (2) a control valve to vary to the flow, and (3) a flow controller to direct the control valve to open or close as necessary to maintain the desired flow.

Micro Motion coriolis mass flow meters have been utilized in past processes with demonstrated flow accuracy and are depicted in the following process descriptions. These instruments are available from Micro Motion, Inc. USA, 7070 Winchester Circle, Boulder, Colo. 80301. These particular instruments use coriolis technology to provide a direct mass flow rate indication (as opposed to a volumetric flow indication which must be converted to mass units and be corrected for temperature variation) and also contain a flow signal transmitter used to provide a feedback flow signal to a control system computer. The size specification of the mass meter depends on the magnitude of the desired flow, density/viscosity characteristics of the flowing liquid, and pressure drop inherent with the associated piping.

Typical automatic control valves are pneumatically actuated to raise/lower a stem in the valve body. A precisely machined and specifically contoured "trim" is attached to the stem and internally resides in the flow path within the valve body. The trim serves to vary the size of the flow orifice as the stem moves up and down. The trim size is specified to provide a particular flow range for a given pressure drop across the valve. The pneumatic actuation signal is typically provided from an I/P device used to convert an electronic signal from a controller (usually measured in milliamps with a 4-20 mA range) to a corresponding pneumatic signal (usually measured in gauge pressure with a 3-15 psig range). Air pressure is supplied to the I/P device which in turn supplies a precise pressure to actuate the valve. The I/P device is usually calibrated at 0-100% scale of a 4-20 mA electronic signal to correspond to a 3-15 psig pneumatic signal at 0-100% scale of the desired flow range (i.e. 4 mA=3 psig=0 flow, 20 mA=15 psig=100% flow). Depiction of the I/P devices have been omitted in the proposed flow diagrams as they are universally assumed to be required. Size specification of the particular valve depends on the desired pressure drop across the valve, pipe size, and trim selection to provide the desired flow range. Control valves for ½ inch to 1 inch diameter process lines are typically available from Badger Meter, Inc. Industrial Division, 6116 East 15th St., Tulsa, Okla. 74158.

The controller is the heart of the control loop and is usually an electronic "black box" within the control system computer software. Most controllers are one of three types: Proportional (P), Proportional Integral (PI), or Proportional Integral Derivative (PID). The names reflect what type of response action will be taken to adjust the control signal. In depth descriptions of each type will not be provided here. Most flow control loops use a PI controller due to the fast response nature of the flow measurement and control valve.

The overall feedback control loop functions as follows:
A desired flow value (setpoint) is input to the controller. A sensor device measures the current flow (measured variable) and returns the current flow value to the controller. The controller calculates the error between the measured variable and the desired setpoint value. The controller then supplies a signal to the I/P and control valve to vary the position (manipulated variable) of the control valve for either increased or reduced flow to minimize the error between the actual and desired flow values. The determination of how fast or how much to vary the position of the control valve depends on the tuning parameters supplied to the controller for Proportional Integral response. The control loop is "tuned" by changing these parameters to achieve optimal response (error minimization) to process upsets or setpoint changes.

The processes of FIGS. 2 and 3 utilize nested cascade ratio flow control to continuously produce the concentrated liquid biocidal compositions. Cascade ratio control is based on feedback control loops. For this type of control, a primary material stream is controlled at a desired flow setpoint. The flow transmitter that provides feedback response to the controller, usually called the master controller, also sends a flow signal to a ratio controller. This signal becomes the setpoint for a second material stream flow controller and hence the term cascade. This controller, usually called the slave controller, provides a signal to a control valve controlling the flow of a second material stream. A flow element in the second stream measures the flow and returns a signal back to the ratio flow controller. The secondary controller calculates the error between the measured flow value and the remotely supplied setpoint. The secondary controller then provides a signal to vary the second control valve accordingly to maintain the secondary flow as a ratio of the primary flow.

The flow controllers are usually contained as individual block elements within the operating software of a process control computer system. A typical control system is a Foxboro I/A Distributed Control System (DCS).

FIG. 2

Reference will now be made specifically to FIG. 2. This Figure describes a flow control system in which the alkali metal sulfamate formed is sodium sulfamate using sodium hydroxide as the base. However, the system is applicable to use of other alkali metal sulfamates formed using water-soluble bases other than sodium hydroxide. The control basis for the process of FIG. 2 is the nested cascade ratio flow control system employed to simultaneously control chlorine flow rate at a set ratio of a desired bromine flow rate. The combined total bromine/chlorine flow rate is then used to simultaneously control the sodium sulfamate flow rate at a desired ratio of the bromine/chlorine flow rate.

One of the vessels depicted is used to neutralize sulfamic acid to form sodium sulfamate. The desired water charge is added to such vessel. Solid sulfamic acid is charged from individual bags or supersacks to the same vessel with agitation to form an aqueous sulfamic acid slurry solution. An aqueous solution of 25% caustic (NaOH) is fed to the sulfamic acid solution to form aqueous sodium sulfamate. The sodium sulfamate solution is then transferred via pump pressure to the second depicted vessel which is equipped with a pump around circulation loop. A feed stream from the circulation loop is used to feed sodium sulfamate to the remaining continuous portion of the process.

Liquid bromine is fed continuously from a pressurized bromine supply vessel. The bromine (primary stream) flows through a Micro Motion mass flow meter then through an automatic control valve. The desired bromine flow rate is input as a setpoint to the bromine flow controller (master controller). The flow controller then sends a signal to the bromine control valve to vary the flow to maintain the desired flow rate. A one-way check valve is installed downstream of the bromine control valve to prevent back flow into the bromine supply line.

Liquid chlorine is supplied continuously from a bulk supply vessel either by tank vapor pressure or augmented with nitrogen pressure. Chlorine (secondary stream) flows through a Micro Motion mass flow meter then through an automatic control valve. The flow rate signal from the primary bromine mass flow meter/transmitter is sent to the chlorine ratio flow controller as a remote setpoint. The chlorine ratio flow controller then sends a signal to the chlorine control valve to vary the chlorine flow as a ratio of the bromine flow rate. A one-way check valve is installed downstream of the chlorine control valve to prevent back flow into the chlorine supply line.

The bromine and chlorine lines are brought together into a multi-element static mixer, commonly available from Koch Engineering Company, Inc., P.O. Box 8127, Wichita, Kans. 67208. The static mixer functions to provide dynamic in-line mixing with minimal linear space and no moving parts.

The flow rate signals from both the bromine and chlorine mass flow meters/transmitters are output to the computer control system and are summed together to obtain an overall flow rate of both streams. The overall flow rate value is then sent to a second ratio flow controller as a remote set point for the sodium sulfamate stream. The sodium sulfamate stream is supplied from pump pressure from the pump around circulation loop on the second depicted vessel. This stream flows through a Micro Motion mass flow meter then through an automatic control valve. The flow rate signal from the sodium sulfamate mass flow meter/transmitter is sent to the ratio controller which sends a signal to the control valve to vary the sodium sulfamate flow rate as a ratio of the combined bromine/chlorine flow rate. A one-way check valve is installed downstream of the sodium sulfamate control valve to prevent back flow into the sodium sulfamate supply line.

The sodium sulfamate stream and the combined bromine/chlorine stream exiting the first static mixer are brought together into a second multi-element static mixer. The exiting stream from this static mixer is the desired concentrated liquid biocidal composition, which is sent to a bulk product storage tank.

The advantage of the process flow system of FIG. 2 is that preparation of the sodium sulfamate solution can take place outside of the continuous portion of the process. The water, caustic, and sulfamic acid can be charged as normal batch operations with a large solution being prepared in advance and transferred to the sodium sulfamate feed vessel as required. Additionally the entire process can be controlled by entering a single set point for the desired bromine flow rate. All other material flow rates are obtained as internal remote setpoints. It should be noted that the magnitude of the desired flow ratios for the ratio controllers are typically configured within the individual controller as set parameters as opposed to user entered setpoint values.

FIG. 3

The process flows and control systems of FIG. 3 will now be considered. As is the case of FIG. 2, FIG. 3 is described with reference to a flow control system in which the alkali metal sulfamate is sodium sulfamate formed using sodium hydroxide as the base. However, the system is applicable to the use of any water-soluble alkali metal sulfamate formed using other water-soluble alkali metal bases.

The process of FIG. 3 eliminates the second vessel depicted in FIG. 2, the vessel that is used in FIG. 2 as a sodium sulfamate supply vessel. The overall system of FIG. 3 includes additional control elements for the single vessel of FIG. 3 to continuously neutralize sulfamic acid and to feed sodium sulfamate solution to the process. The continuous mixing process to feed bromine, chlorine, and sodium sulfamate remain as in FIG. 2.

In the process of FIG. 3, an aqueous solution of 25% caustic is fed to the reaction vessel depicted through a Micro Motion mass flow meter then through an automatic control valve. A desired caustic flow rate setpoint is entered into the caustic flow rate controller. The caustic flow controller then sends a signal to the control valve to suitably vary the caustic flow in order to maintain the desired flow rate. The flow rate signal from the caustic mass flow meter/transmitter is also sent as a remote setpoint to a water ratio flow controller.

Water is fed to the reaction vessel depicted through a Micro Motion mass flow meter then through an automatic control valve. The water ratio controller then sends a signal to the control valve to vary the water flow as a ratio of the caustic flow rate.

Solid sulfamic acid is charged to the depicted vessel at a flow rate consistent with the water/caustic flow to provide the necessary sulfamic acid/sodium sulfamate concentration within the vessel. A Rotolock valve is typically installed in the solids charge line to accomplish solids feeding at a set flow rate. This type of valve is a multi-vane rotary valve coupled to a direct current (DC) motor with a speed controller. The motor speed is adjusted to provide the desired solids feed rate (as determined from separate calibration for speed vs. flow rate). The Rotolock system can be further enhanced by instrumenting for automatic feedback control. This is usually accomplished by mounting the solids hopper feeding the Rotolock valve on weigh cells. For this setup, a desired solids feed rate is entered into a feed controller. The controller sends a signal to the motor to either speed up or slow down to achieve the desired flow rate. The solids flow rate is obtained by internal calculation of the loss-in-weight over time from the solids hopper. If the sulfamic acid charge system was instrumented for automatic control, the logical extension would be to send the solids flow rate signal to the caustic flow controller as a remote setpoint for the desired caustic flow. Since this step consists of a neutralization reaction, a certain amount of residence time is required for complete neutralization to sodium sulfamate. The available information indicates that the neutralization is mass transfer limited by the caustic feed rate and also by the cooling capacity of the reactor. This neutralization is somewhat exothermic and requires cooling to remove the generated heat. A pump around circulation loop is one way to provide sufficient residence time if the required sodium sulfamate flow rate for the rest of the process is not excessively large.

Bromine, chlorine, and sodium sulfamate are then fed identically as in the process of FIG. 2. Sodium sulfamate is fed continuously by taking a feed stream from the pump around circulation loop from the depicted reaction vessel and flowing through a mass flow meter and control valve. The desired flow rate is obtained as a remote setpoint to a ratio flow controller from the summation of the total bromine/chlorine feed rate.

The advantage to the process of FIG. 3 is the elimination of one process vessel. This elimination is offset, at least to some extent, by the expense of additional control elements required for feeding water, caustic, and sulfamic acid.

It will now be understood and appreciated that the automatic flow control systems described herein can be effectively utilized in process layouts other than those depicted in FIGS. 2 and 3. One example of one such other process layouts is described with reference to FIG. 1.

The following Examples are presented for purposes of illustration and not limitation.

EXAMPLES

Various compositions were prepared and the active bromine content of the resultant compositions was determined analytically. The conditions used and results obtained (observations on odor and vapor, and initial contents of active bromine in the solutions) are summarized in Table 1.

Table 1—Data on Prepared Sulfamic Acid Stabilized Bromine Solutions

TABLE 1

Data on Prepared Sulfamic Acid Stabilized Bromine Solutions

| Ex. No. | Halogen | pH | $SA_{eq}$ | Odor and Vapor Comments | Active $Br_2$, wt % |
|---|---|---|---|---|---|
| 1 | $Br_2$ | 13.0 | 1.42 | Slight sweet smell, no observed vapor | 12.4%* |
| 2 | $Br_2$ | 7.0 | 1.48 | Slight Br odor, no fuming | 13.4%* |
| 3** | BrCl | 7 | 0.92 | Strong Br odor, slight fuming | 11.2% |
| 4 | $Br_2$ | 13.0 | 1.15 | Slight sweet smell, no observed vapor | 19.6% |
| 5 | $Br_2$ | 7.0 | 1.13 | Moderate Br odor, no fuming | 26.7% |
| 6 | BrCl | 12.5 | 0.94 | Slight sweet smell, no observed vapor | 18.0% |
| 7 | BrCl | 12.8 | 1.41 | Slight sweet smell, no observed vapor | 17.6% |

$SA_{eq}$ = Sulfamic acid to halogen mole ratio.
*Measured with Hach spectrometer; all others titrated using starch-iodine-sodium arsenite method.
**Comparative example.
The specific details for Examples 3-7 of the Table are given below.

$SA_{eq}$=Sulfamic acid to halogen mole ratio.

* Measured with Hach spectrometer; all others titrated using starch-iodine-sodium arsenite method.

** Comparative example.

The specific details for Examples 3-7 of the Table are given below.

Example 3

Bromine Chloride, Caustic and Sodium Sulfamate at Neutral pH

A 1 liter flask was charged with 52.0 g of sulfamic acid and 250 g of water. Sodium sulfamate was prepared by adding 60.0 g of 50% sodium hydroxide to the stirred slurry. Bromine chloride was prepared by adding 20 g of chlorine to 47.0 g of bromine. This bromine chloride was then co-fed with 210 g of 25% sodium hydroxide to maintain the pH between 6 and 8. 5 mL of 1 M Hydrochloric Acid were added to bring the final pH to approximately 7±0.5. The solution, which contained some solids, was transferred to an amber bottle for storage. Starch-iodine titration of a sample of the solution indicated that it had an active bromine concentration of 11.2%.

Example 4

Bromine, Caustic (50% Sodium Hydroxide) and Sodium Sulfamate

A 500 mL flask was charged with 26.0 g of sulfamic acid and 50 g water. To this slurry was added 35.0 g of 50% sodium hydroxide. As the acid was converted to the sodium salt, it dissolved into the aqueous solution more readily. Bromine (37.0 g) and 50% sodium hydroxide (30.0 g) were co-fed into the solution at a rate which maintained the pH between 11 and 13. After all of the bromine and caustic had been added, the contents were transferred to an amber bottle for storage. Starch-iodine titration of a sample of the solution indicated that it had an active bromine concentration of 19.6%. Analysis of the bromine solution after 6 weeks of storage at ambient temperature indicated that it still contained more than 95% of its active bromine content.

Example 5

Bromine, Caustic and Sodium Sulfamate at Neutral pH

A 500 mL flask was charged with 26.0 g of sulfamic acid and 50 g of water. To this stirred slurry was added 30.9 g of 50% sodium hydroxide, which raised the initial pH to approximately 12. The sulfamic acid then dissolved into solution. Bromine (37.7 g) was fed into the solution until the pH dropped to approximately 7, when 50% sodium hydroxide (10.9 g) was co-fed to maintain the pH between 6 and 9. 5 mL of 0.01 N sodium hydroxide was used to bring the final pH to approximately 7±0.5. The contents were then transferred to an amber bottle for storage. Starch-iodine titration of a sample of this solution indicated that it had an active bromine content of 26.7%. Analysis of the solution after six weeks of storage at ambient temperature indicated that the stabilized bromine solution still contained more than 95% of its active bromine content.

Example 6

Bromine Chloride, Caustic and Sodium Sulfamate

A 1 liter flask was charged with 107 g of sulfamic acid and 200 g of water. Sodium sulfamate was prepared by adding 93.9 g of 50% sodium hydroxide to the stirred slurry. Bromine chloride was prepared by adding 39 g of chlorine to 96.0 g of bromine. This bromine chloride was the co-fed with 319 g of 50% sodium hydroxide to maintain the pH between 11 and 13. After stirring for an additional 30 minutes, the solution, which contained some solids, was transferred to an amber bottle for storage. Starch-iodine titration of a sample of the solution indicated that it had an active bromine concentration of 18.0%. Analysis of the solution after three weeks at ambient temperature indicated that the stabilized bromine solution still contained more than 90% of its active bromine content.

Example 7

Bromine Chloride, Caustic and Sodium Sulfamate; Larger Scale

A 5 liter flask was charged with 470 g of sulfamic acid and 900 g of water. Sodium sulfamate was prepared by adding 436 g of 50% sodium hydroxide to the stirred slurry. Bromine chloride was prepared by adding 120 g of chlorine to 276 g of bromine. This bromine chloride was the co-fed with 1723 g of 50% sodium hydroxide to maintain the pH between 12 and 13. After stirring for an additional 60 minutes, the orange, clear solution was transferred to an polyethylene bottle for storage. Starch-iodine titration of a sample of the solution indicated that it had an active bromine concentration of 17.6%.

Even though the claims hereinafter may refer to substances, components and/or ingredients in the present tense ("comprises", "is", etc.), the reference is to the substance, component or ingredient as it existed at the time just before it was first contacted, blended or mixed with one or more other substances, components and/or ingredients, or if formed in solution, as it would exist if not formed in solution, all in accordance with the present disclosure. It matters not that a substance, component or ingredient may have lost its original identity through a chemical reaction or transformation during the course of such contacting, blending, mixing, or in situ formation, if conducted in accordance with this disclosure.

Each and every patent or publication referred to in any portion of this specification is incorporated in toto into this disclosure by reference, as if fully set forth herein.

This invention is susceptible to considerable variation in its practice. Therefore the foregoing description is not intended to limit, and should not be construed as limiting, the invention to the particular exemplifications presented hereinabove. Rather, what is intended to be covered is as set forth in the ensuing claims and the equivalents thereof permitted as a matter of law.

The invention claimed is:

1. A process for producing an aqueous biocidal composition by adding bromine chloride to an alkali metal sulfamate solution formed from water, sulfamic acid and alkali metal base, wherein an atom ratio of nitrogen to active bromine from the bromine chloride and alkali metal sulfamate solution used to produce the aqueous biocidal composition is greater than 0.93, wherein the pH of said alkali metal sulfamate solution is in the range of about 13.0 to about 14.0 during said bromine chloride addition, and wherein a sufficient amount of said bromine chloride is added to the solution such that the aqueous biocidal composition produced has an active bromine content of at least 100,000 ppm.

2. The process of claim 1, wherein a sufficient amount of said bromine chloride is added to the solution such that the aqueous biocidal composition produced has an active bromine content in the range of about 120,000 ppm (wt/wt) to about 180,000 ppm (wt/wt).

3. The process of claim 1, wherein an atom ratio of nitrogen to active bromine from the bromine chloride and alkali metal sulfamate solution used to produce the aqueous biocidal composition is in the range of about 1.0 to about 1.4.

4. The process of claim 1, wherein the pH of said alkali metal sulfamate solution is in the range of about 13.0 to about 14.0 during said bromine chloride addition by feeding additional alkali metal base.

5. The process of claim 4, wherein an atom ratio of nitrogen to active bromine from the bromine chloride and alkali metal sulfamate solution used to produce the aqueous biocidal composition is in the range of about 1.0 to about 1.4.

6. A stabilized aqueous biocidal formulation preparable by adding bromine chloride to an alkali metal sulfamate solution formed from water, sulfamic acid and alkali metal base, wherein said aqueous biocidal solution has an atom ratio of nitrogen to active bromine greater than 0.93, wherein the pH of said alkali metal sulfamate solution is in the range of about 13.0 to about 14.0 during said bromine chloride addition, and wherein said aqueous biocidal solution has an active halogen content of at least 100,000 ppm measured as $Br_2$.

7. The stabilized aqueous biocidal formulation of claim 6, wherein said aqueous biocidal solution has an active halogen content in the range of about 120,000 ppm (wt/wt) to about 180,000 ppm (wt/wt) measured as $Br_2$.

8. The stabilized aqueous biocidal formulation of claim 6, wherein said aqueous biocidal solution has an atom ratio of nitrogen to active bromine in the range of about 1.0 to about 1.4.

9. The stabilized aqueous biocidal formulation of claim 6, wherein the pH of said alkali metal sulfamate solution is in the range of about 13.0 to about 14.0 during said bromine chloride addition by feeding additional an alkali metal base.

10. The stabilized aqueous biocidal formulation of claim 9, wherein said aqueous biocidal solution has an atom ratio of nitrogen to active bromine in the range of about 1.0 to about 1.4.

* * * * *